United States Patent [19]

Evans et al.

[11] Patent Number: 5,578,483
[45] Date of Patent: Nov. 26, 1996

[54] RECEPTOR TRANSCRIPTION-REPRESSION ACTIVITY COMPOSITIONS AND METHODS

[75] Inventors: Ronald M. Evans, La Jolla, Calif.; Stanley M. Hollenberg, Seattle, Wash.; Anthony E. Oro, San Diego, Calif.

[73] Assignee: The Salk Institute for Biological Studies, La Jolla, Calif.

[21] Appl. No.: 691,043

[22] Filed: Jun. 21, 1991

Related U.S. Application Data

[63] Continuation-in-part of Ser. No. 289,561, filed as PCT/US89/05859 Dec. 26, 1989, abandoned.

[51] Int. Cl.$^6$ .............................. C12N 5/16; C12N 15/85; C07K 14/705
[52] U.S. Cl. .................... 435/240.2; 435/320.1; 530/350
[58] Field of Search ...................... 530/350, 399; 435/69.7, 240.1, 240.2, 320.1, 69.4; 935/2, 23

[56] References Cited

U.S. PATENT DOCUMENTS

| | | |
|---|---|---|
| 4,892,871 | 1/1990 | Nathanson . |
| 4,981,784 | 1/1991 | Evans et al. ............................. 435/6 |

OTHER PUBLICATIONS

Lavin et al., The Thyroid Hormone Receptor Binds to Multiple Domains of the Rat Growth Hormone 5'-Flanking Sequence, The Journal of Biological Chemistry vol. 263:9418-9426 (1988).

Thompson and Evans, Trans-activation by thyroid hormone receptors: Functional parallels with steroid hormone receptors, Proc. Natl. Acad. Sci. USA vol. 86:3493-3498 (1989).

Damm et al, Protein encoded by v-erbA functions as a thyroid-hormone receptor antagonist, Nature vol. 339:593-597 (1989).

Evans 1988 Science vol. 240:889-895.

Hollenberg et al 1987 Cell. 49:39-46.

Giguere et al. 1987 Nature 330:624.

Picard & Yamamoto 1987 EMBO J. 6(11): 3333-3340.

Primary Examiner—Robert A. Wax
Assistant Examiner—K. Cochrane Carlson
Attorney, Agent, or Firm—Pretty, Schroeder, Brueggemann & Clark; Stephen E. Reiter; Robert T. Ramos

[57] ABSTRACT

Disclosed is an analysis of domains of receptors of the steroid/thyroid hormone superfamily, and particularly of the glucocorticoid receptor, to identify requirements for the trans-acting transcriptional repression activities of the receptors. Based on the analysis, certain novel receptor analogs are provided, as are various novel DNAs, expression vectors, cells and transgenic animals as well as novel methods of using trans-acting transcription-repressing analogs of the receptors in various applications. These applications include gene therapy, screening of cells in culture or transgenic animals for compositions effective to treat various diseases due to inability to properly respond to hormones of the steroid or thyroid hormone group, and screening of cells in culture for ligands that are capable, upon binding to one of the receptors, to activate its trans-acting transcription activating and trans-acting transcription-repressing activities.

8 Claims, 4 Drawing Sheets

RECEPTOR TRANSCRIPTION-REPRESSION ACTIVITY COMPOSITIONS AND METHODS

This application is a continuation-in-part of Ser. No. 07/289,561, filed as PCT/US89/05859 Dec. 26, 1989, now abandoned.

RELATED APPLICATIONS

Receptors, assay methods, and other subject matter pertinent to the subject matter of the present specification are described in the following patent applications, which are incorporated herein by reference: PCT International Publication No. WO 88/03168; European Patent Application Publication No. 0325849; and PCT International Application No. US89/05419, filed Nov. 29, 1989 (see Hollenberg and Evans, *Cell;* 55, 899 (1988).

FIELD OF THE INVENTION

The present invention relates to the trans-acting transcription-repression activity of hormone receptors of the steroid/thyroid hormone receptor superfamily. More particularly, it relates to the identification and characterization of amino acids and amino acid sequences in such hormone receptors, especially the steroid hormone receptors and including those of the human species, that are responsible for such repressor activity, receptor analogs based on such identification and characterization, and preparation and use of such receptor analogs.

Receptor analogs, which have been discovered to have transcription-repression activity greater than that of the corresponding, naturally occurring receptor, and DNAs from which such analogs can be expressed in mammalian cells, may advantageously be employed to provide model cellular and transgenic-animal systems of diseases, including human diseases, associated with the inability to respond properly to the hormone, which is the natural ligand of the naturally occurring receptor. These model systems, in turn, may be employed advantageously to screen for compositions that are effective in treating such diseases.

The receptor analogs identified in connection with the invention, and DNAs from which such analogs can be expressed in mammalian cells, may also find use in gene therapy to treat diseases associated with the inability to respond properly to the hormone, which is the natural ligand of the naturally occurring receptor corresponding to the analog.

Finally, the receptor analogs, whose transcription-repression activity is ligand- (e.g., hormone-) dependent, DNAs from which such analogs can be expressed and cells in which such DNAs are expressed, can be employed in functional assay systems, such as those described in the aforementioned patent applications, to screen for ligands that are effective in inducing the activities of the naturally occurring receptor corresponding to the analog.

BACKGROUND OF THE INVENTION

The applications cited supra disclose, inter alia, the characterization and preparation of various hormone and hormone-like receptors, including the glucocorticoid, mineralocorticoid, thyroid hormone, and retinoic acid receptors, and analogs of such receptors. These receptors are members of the steroid/thyroid hormone superfamily of receptors. This superfamily is now known, from numerous publications in the art which have described details of such receptors and DNAs that encode them, to include also, inter alia, the estrogen receptor, the progesterone receptor, and the vitamin D3 receptor.

In PCT International Application No. US89/05419 (corresponding to U.S. patent application Ser. No. 278,614, filed on 30 November 1988) are disclosed hormone or hormone-like receptor analogs, for example, analogs of steroid receptors, thyroid hormone receptors, and retinoic acid receptors, including those of the human species, where advantage is provided by enhancement, over that of the corresponding naturally occurring receptor, of the trans-acting, transcription-activation or transcription-enhancement activity. Such enhancement is provided by changes in domains, of the naturally occurring receptors, that were found to be necessary for the transcription-activation or transcription-enhancement activities of the receptors.

It is known, for example, that the glucocorticoid receptor belongs to the large, steroid/thyroid hormone superfamily of ligand-dependent, transcription factors that have diverse roles in homeostasis, reproduction, development, growth, function of the immune system and function of the central and peripheral nervous systems, among others. Comparison of complementary DNAs encoding receptors of this superfamily, as well as mutational analyses of these DNAs, have identified certain functional domains within the receptor molecules responsible respectively for DNA binding, hormone binding and nuclear localization. See Evans, et al., *Science* 240, 889 (1988) for a review of this subject matter. In the case of the glucocorticoid receptor, the so-called DNA binding domain spans some sixty-six amino acids and is highly conserved among various species and this domain has been found to be required in order to activate transcription. See Hollenberg, et al., *Cell* 49, 39 (1987), Miesfeld, et al., *Science* 236, 423 (1987), Danielsen, et al., *Mol.Endo* 1, 816 (1987), Kumar, et al., *Cell* 51, 941 (1987), Gronemeyer, *EMBO J.* 6, 3985 (1987), and Waterman, et al., *Mol.Endo* 2, 14 (1988). This region has been found to contain nine invariant cysteine residues and, although the contribution of each cysteine residue to overall function as well as the actual structure of this domain, remain unknown, it has been proposed that these cysteine residues coordinate two zinc ions to form two DNA-binding, so-called "zinc-finger," domains which result in a tertiary structure thought responsible for localization and binding of the glucocorticoid receptor to the requisite DNA site. Similar zinc-finger structures are present in other receptors of the steroid/thyroid hormone receptor superfamily. See Klug, et al., *Tr.Biochem.Sci* 12, 464 (1987), Bens, et al., *Cell* 52, 1 (1988), and Evans, supra.

In a location nearer the carboxyl-terminal end of the receptor molecule, distal from the DNA binding region of the molecule, is the so-called ligand-binding domain. In the absence of ligand (e.g., hormone or hormone-analog which complexes with the receptor at the ligand-binding domain), the ligand-binding domain functions to block transcription-affecting activity of the receptor. Thus, presence of the requisite hormone relieves the inhibition of the receptor to such activity. Deletion of the ligand-binding domain from a receptor of the steroid/thyroid hormone superfamily has been found to produce a hormone-independent transcription activator. See Godowski, et al., *Nature* 325, 365 (1987), Hollenberg, et al., supra, Kumar, et al., supra, Danielsen et al., supra, and Adler et al., *Cell* 52, 685 (1988).

In contrast to these two domains, the domain of a receptor lying towards the amino-terminal region from the DNA binding domain is poorly understood both as to structure and function. This domain nearer the amino-terminus is extremely variable both in size and in composition among the various receptors. See Evans, supra. The domain may contribute to the heterogeneity of receptor function, despite the overall similarity otherwise of the receptors of the superfamily. See Kumar et al., supra, and Tora et al., 333, 185 (1988).

Despite extensive analysis, some of which has been reported in the scientific literature, the region(s) that are responsible (in conjunction with the DNA binding of the receptor) for the transcription activation or enhancement caused by a receptor remains poorly characterized. Transcription-activation (or transcription-enhancement) domains can be defined as regions of a receptor molecule that, when combined with the DNA binding functional domain, increase productive transcription initiation by RNA polymerases at a promoter affected by the receptor. See Sigler, *Nature* 333, 210 (1988), Brent et al., *Cell* 43, 729 (1985), Hope et al., *Cell* 46, 885 (1986), Ma et al., *Cell* 48, 847 (1987), Ma et al., *Cell* 51, 113 (1987), Lech et al., *Cell* 52, 179 (1988), and Hope et al., *Nature* 333, 635 (1988).

Previous research on the human glucocorticoid receptor by linker scanning mutagenesis identified two regions outside of the DNA binding region having a role in transcription activation. These regions were defined as $tau_1$ and $tau_2$. Giguere et al., *Cell* 46, 645 (1986). Further research from these laboratories has also resulted in the report of a co-localization of transcription-activation and DNA-binding functions. See Hollenberg et al., supra, Miesfeld, et al., supra, Danielsen et al., Supra, and Waterman et al., supra. As a composite, this research has given rise merely to a picture, for a receptor of the steroid/thyroid hormone superfamily, that is becoming increasingly modular, with discrete domains, each contributing to the functions of ligand-binding, DNA-binding and "trans-activation" (by which is meant, herein, trans-acting transcription-activation (or enhancement). However, the picture based upon extant literature does not adequately portray the dynamic nature of the activities of the steroid/thyroid hormone receptors and how the various domains participate in the cascade of events initiated by ligand-binding and consummated by promoter-specific trans-activation.

Further, although previous research has identified functional "domains", there has been little systematic effort to identify amino acids and sequences thereof in the receptor molecules that correspond to these domains and contribute to the activities identified for the domains. Thus, the previous identification of steroid receptor trans-activation regions resulted only from a demonstrated loss of activity via deletion or insertional mutagenesis, but in no case have the properties of the regions themselves been confirmed in assays that reflect a dominant gain of function. See also Ptashne, *Nature* 335, 683 (1988).

Thus, Godowski et al., *Science* 241, 812 (1988), report results that show that the glucocorticoid receptor contains at least one "enhancement domain" other than that overlapping the segment of DNA to which the receptor binds (i.e., the glucocorticoid response element or "GRE") and that this second domain occupies a region near the receptor amino-terminus. Similarly, Webster et al., *Cell* 54, 199 (1988) report on an inducible transcription activation function of the estrogen and glucocorticoid receptors, and these researchers speculate that the relative positions of the ligand-binding and DNA-binding domains are, not important for the trans-activation by the receptor. Yet, these researchers admit that they have no definition of the exact location and nature of what they call the "hormone-inducible activating domain" responsible for this inducible transcription activation function and they provide no characterization of the domain and no description of how, in molecular terms, it might contribute to trans-activation.

As a starting point for the present invention, Giguere et al., supra, demonstrated loss of activity in mutants of the glucocorticoid receptor, provided by DNAs resulting from random site-mutagenesis at several locations in a cDNA encoding the receptor. The loss of activity observed by Giguere et al. in this study was in an assay measuring transcription activity from a promoter operatively associated with a GRE so that transcription from the promoter was affected by glucocorticoid hormone receptor binding to the GRE. As a follow-up, Hollenberg et al., supra, deleted regions in the receptor molecule, again demonstrating overall loss of transcription activity induced by such removal of stretches of amino acids.

In PCT International Application No. US89/05419, filed Nov. 29, 1989, and corresponding to U.S. patent application Ser. No. 278,614, filed Nov. 30, 1988, as well as Hollenberg and Evans, supra, domain(s) responsible for trans-activation ("trans-activation" domains, i.e., domains responsible for the trans-acting transcription-activating activity of an hormone receptor at a promoter whose transcription activity is affected by the receptor) was (were) identified and characterized, and the characterization of such domain(s) in respect of amino acid composition and sequence was developed, to explore the functional interaction of the domain(s) with both the DNA-binding and ligand-binding domains of a given receptor, and finally, to exploit such knowledge to provide receptor analogs with increased trans-activating activity in comparison with that of the corresponding, naturally occurring receptor.

The present invention makes further use of the information provided by the invention disclosed in PCT International Application No. US89/05419 and Hollenberg and Evans, supra.

The human glucocorticoid receptor (hGR) has served as a prototype, model receptor for studying regulation of gene transcription by receptors of the steroid/thyroid hormone superfamily. The DNA-binding and ligand-binding functional domains of the hGR were first defined and the corresponding domains of other members of the superfamily identified in part on the basis of the results with the hGR. Further, it has been found that these DNA-binding and ligand-binding domains are modular in that, for example, the ligand-binding domain of a first hormone receptor (e.g., hGR) may be swapped with a ligand-binding domain of a second hormone receptor (e.g., hTR (human thyroid hormone receptor)) to produce a hybrid receptor the DNA-binding domain of which retains specificity for its cognate response element (GRE) in DNA, but which trans-activates only in the presence of the hormone (thyroid hormone, in this case) specific for the second receptor. Thus, reference herein to the "naturally occurring" receptor corresponding to a receptor analog of the invention means the naturally occurring receptor with the DNA-binding domain that is closest in primary sequence to the DNA-binding domain of the analog.

While trans-activation by the hGR (and other receptors of the steroid/thyroid hormone receptor superfamily) has been examined and elucidated in considerable detail, relatively little is known about "trans-repression" by the hGR or other receptors of the superfamily (i.e., trans-acting repression of transcription from a promoter, transcription from which is subject to repression by such a receptor).

Among their many effects in development and the reproductive, hepatic, metabolic, nervous and other systems, glucocorticoid hormones help determine neural crest cell fate in the developing sympathoadrenal system in part by repressing the induction of neural-specific genes (See Stein et al., *Dev Bio* 127, 316 (1988) and Anderson et al, *Cell* 47, 1079 (1986).) Also glucocorticoid hormones modulate the hypothalamic-pituitary-adrenal axis by inhibiting second messenger-induced peptide hormone induction. Recently, Akerblom et al. (*Science* 241, 350 (1988)) showed that the hGR negatively regulates (i.e., represses transcription from) the cAMP-inducible alpha glycoprotein hormone promoter in asteroid- and DNA-binding dependent manner. Wild-type expression is initiated by transcription from a promoter of Just 168 base pairs (termed alpha168). Basal expression of alpha glycoprotein hormone in placental cells is mediated by factors bound to a 36 base pair palindromic cyclic AMP response element (CRE) cooperating with proteins binding to a 25 base pair tissue-specific element (TSE). Expression may be further enhanced through the CRE by the elevation of intracellular cyclic AMP levels. The hGR represses both the basal and cAMP enhanced transcription in a glucocorticoid-dependent fashion. The transacting elements to which the hGR binds have been defined and are related to the consensus GRE sequence that has been defined in studies of trans-activation by the hGR. Similar research is reported by Sakai, et al., *Genes and Development* 2, 1144 (1988).

It is an object of the present invention to provide novel hormone or hormone-like receptor analogs that have transacting, transcription-repressing activity, at promoters whose transcription activity is capable of being repressed by the corresponding, native (i.e., naturally occurring) receptor. The novel receptor analogs are characterized in that they possess domains at their C-termini that differ in certain ways from the corresponding domains in the corresponding, native receptors.

It is a further object of the invention to provide novel, model, cellular and transgenic-animal systems of diseases, including human diseases, associated with the inability to respond properly to the hormone, which is the natural ligand of a naturally occurring receptor. It is still a further object of the invention to use these model systems to screen for compositions that are effective in treating such diseases. These cellular and transgenic-animal, model systems employ certain receptor analogs which have been found to have certain trans-repression-related activities, particularly transcription-repression activity greater than that of the corresponding, naturally occurring receptor, and DNAs of the invention, from which such analogs can be expressed in mammalian cells. Novel cells of the invention, including cells in novel transgenic animals of the invention which comprise novel cells of the invention, in which such receptor analogs are expressed will respond aberrantly to the hormone corresponding to the receptor analog because transrepressing activities by the receptors (including the analog-)for the hormone in the cells will aberrantly dominate trans-activating activities by such receptors.

It is a further object of the invention to use receptor analogs, which have been identified to have certain transrepression activities, and DNAs of the invention, from which such analogs can be expressed in mammalian cells, in gene therapy to treat diseases associated with the inability to respond properly to the hormone, which is the natural ligand of the naturally occurring receptor corresponding to the analog. The effect of having the receptor analog in a subset of the cells of a mammal (including a human) treated by such gene therapy, would be to modulate the response of the mammal to the hormone to a more nearly normal response.

The invention has as still another object novel, functional assay systems, which employ the receptor analogs of the invention, whose transcription-repression activity is ligand (e.g., hormone-)dependent, novel DNAs of the invention, from which such analogs can be expressed, and novel cells of the invention, in which such DNAs are expressed, to screen for ligands that are effective in inducing the activities of the naturally occurring receptor corresponding to the analogs. Such functional assay systems to screen for such ligands are described in PCT International Publication No. WO 88/03168 and European Patent Application Publication No. 0 325 849.

SUMMARY OF THE INVENTION

The present invention is based upon an analysis of the structural requirements of the hGR for effecting transrepression. This analysis has revealed that, although deletion of portions of the N-terminus of a hormone receptor (the hypervariable region) may affect transcription repressing activity, potent trans-repressing receptors may be made which lack the entire N-terminal domain. The DNA binding domain is necessary, but not sufficient, for transcriptionrepressor activity. Surprisingly, however, a receptor analog having practically any polypeptide at its C-terminus which is capable of providing sufficient molecular volume will have transcription repressing activity, although preferably the C-terminal domain of a receptor analog employed in accordance with the invention includes a modified ligandbinding domain of a receptor of the steroid/thyroid hormone receptor superfamily, as described herein. Thus, a receptor analog comprising such a C-terminal domain, including one which is not capable of ligand-binding, fused to a DNA-binding domain is a novel receptor analog of the invention.

The present invention supports a mechanism involving primarily steric hindrance for effecting trans-repression by asteroid hormone receptor or another receptor of the steroid/thyroid hormone receptor superfamily, once the receptor is bound to a cognate recognition element in DNA associated with the promoter, the transcriptional activity of which is to be repressed.

The present invention is predicated upon the identification, isolation and characterization of the modular domains of receptors of the steroid/thyroid hormone receptor superfamily, which domains, particularly the C-terminal domain, may be modified, and the N-terminal domain all or partially removed, to create trans-acting transcription-repressing receptor analogs of the invention. We have discovered novel receptor analogs comprising a DNA-binding domain and a modified C-terminal domain, which novel receptors bind to a cognate response element of the DNA-binding domain and, apparently by steric hindrance in the vicinity of the response element, exhibit potent trans-acting transcription repression activity at a promoter operatively located from the response element for such transcription-repression to occur.

It has further been found that the DNA-binding domain is a necessary component in any receptor analog having such repressor activity, although the N-terminal, hypervariable region, is not essential for such repression. In fact, removal of all or part of the N-terminal domain advantageously enhances transcription-repressing activity and decreases transcription-activating activity. Thus, the receptor analogs employed in this invention contain a DNA-binding domain, optionally an N-terminal domain, and a C-terminal domain that is effective to provide (optionally upon ligand-binding) transcription repressing activity. The receptors analogs may be hybrid receptors wherein the DNA-binding domain, N-terminal domain (optional) and ligand-binding domain (C-terminal) are provided from receptors of different classes and/or species. For example, the C-terminus domain of the glucocorticoid receptor, including the human glucocorticoid receptor, can be replaced herein by a portion of the C-terminus of the human mineralocorticoid receptor.

The present invention thus concerns a hormone or hormone-like receptor analog having trans-acting transcription repressor activity ("trans-repressing activity") with respect to a promoter with which it is associated, by virtue of the analog's ability to bind to a cognate response element in DNA upstream of said promoter and block the activity of other transcription factors associated with the promoter. A receptor analog of concern for the present invention, including the novel ones which per se are part of the present invention, can, like a corresponding native receptor, both repress transcription from promoters, whose transcription is repressed by the corresponding naturally occurring receptor, and activate transcription from promoters, whose transcription is activated by the corresponding native receptor. In the preferred receptor analogs, the trans-repressing activity is greater than that of the corresponding native (i.e., naturally occurring) receptor at the repressed promoters and the trans-activating activity is lower than that of the corresponding native receptor at the activated promoters.

Thus, a novel receptor analog of the invention is a trans-repressing analog of a first receptor of the steroid/thyroid hormone superfamily of receptors, said analog comprising (1) a DNA-binding domain, through which the analog is capable of binding to a recognition element of said first receptor, when said recognition element is operatively associated with a promoter for trans-repression of the promoter by said first receptor; (2) a carboxy-terminal domain which is the carboxy terminal domain of a second receptor of the steroid/thyroid hormone superfamily of receptors, said second receptor being different from said first receptor, or which is a polypeptide, which has less than about 60% amino acid identity over its entire length, if shorter than the carboxy-terminal domain of said first receptor, or over any of its segments with the same length as the carboxy-terminal segment of said first receptor, provided that the polypeptide has about as many amino acids (at least about 90% as many) as the carboxy-terminal domain of said first receptor; and (3) if the carboxy-terminal domain is the carboxy-terminal domain of a second receptor, an N-terminal domain that differs from the N-terminal domain of the first receptor by the deletion of a plurality of amino acids.

The present invention is further directed to the preparation of receptor analogs of the invention, and otherwise of concern for the methods of the invention, via recombinant DNA technology in all relevant aspects, including a DNA molecule that is a recombinant DNA molecule or a cDNA molecule consisting of a sequence encoding a receptor analog, and to requisite expression vectors harboring such DNA operatively for expression thereof and comprising expression control elements operative in the recombinant hosts selected for the expression, to recombinant host cells transfected with such operative expression vectors, and to transgenic, non-human animals, preferably mammals such as rats or mice, which harbor in some of their cells DNA from which a the receptor analog is expressed.

The invention is further directed to novel applications, described above, in various screening and therapeutic uses, of trans-repressing receptor analogs, DNAs that encode such analogs and from which the analogs can be expressed. particularly in mammalian cells, cells in which the analogs are expressed, and transgenic animals in some cells of which the analogs are expressed.

Thus, for example, the invention encompasses a novel, non-human transgenic mammal, which has symptoms of a disease due to inability to properly respond to a steroid or thyroid hormone, said animal having at least a subset of its cells in which are expressed an analog of a receptor for said hormone, said analog having trans-repression activity greater than that of said receptor and trans-activation activity less than that of said receptor.

DETAILED DESCRIPTION OF THE INVENTION

Numbers to the left of the diagrams of the various mutant receptors, when preceded by a delta, indicate amino acids immediately N-terminal and immediately C-terminal, respectively, of those deleted in the various mutants and, when accompanied by an asterisk (and, usually, preceded by an I), indicate the amino acid at which the mutant receptor is truncated. The mutant at the bottom of the Figure entails a deletion and a truncation. In the table to the right of the diagrams of the wt and mutant receptors, the relative activities of the receptors in trans-repression at the alpha168 transcription regulatory region ("repression") and trans-activation at the mouse mammary tumor virus LTR transcription regulatory region ("activation") are listed for both experiments in the presence of hormone (dexamethasone) and experiments in the absence of hormone. For each receptor mutant, relative activity in trans-repression is determined taking the CAT activity observed (normalized for transfection efficiency) using only Rsv-promoter-containing control plasmid as representing 0% activity in trans-repression and that observed using wild-type receptor as representing 100% activity in trans-repression. The data in the table are +/− the standard error of the mean from the several experiments with each of the mutants. A single asterisk indicates trans-repression activity is less than 10 percent of wild type trans-repression activity on the alpha168 promoter. A double asterisk indicates less than 1 percent of trans-activation activity on the MMTV LTR promoter.

Figure 2:
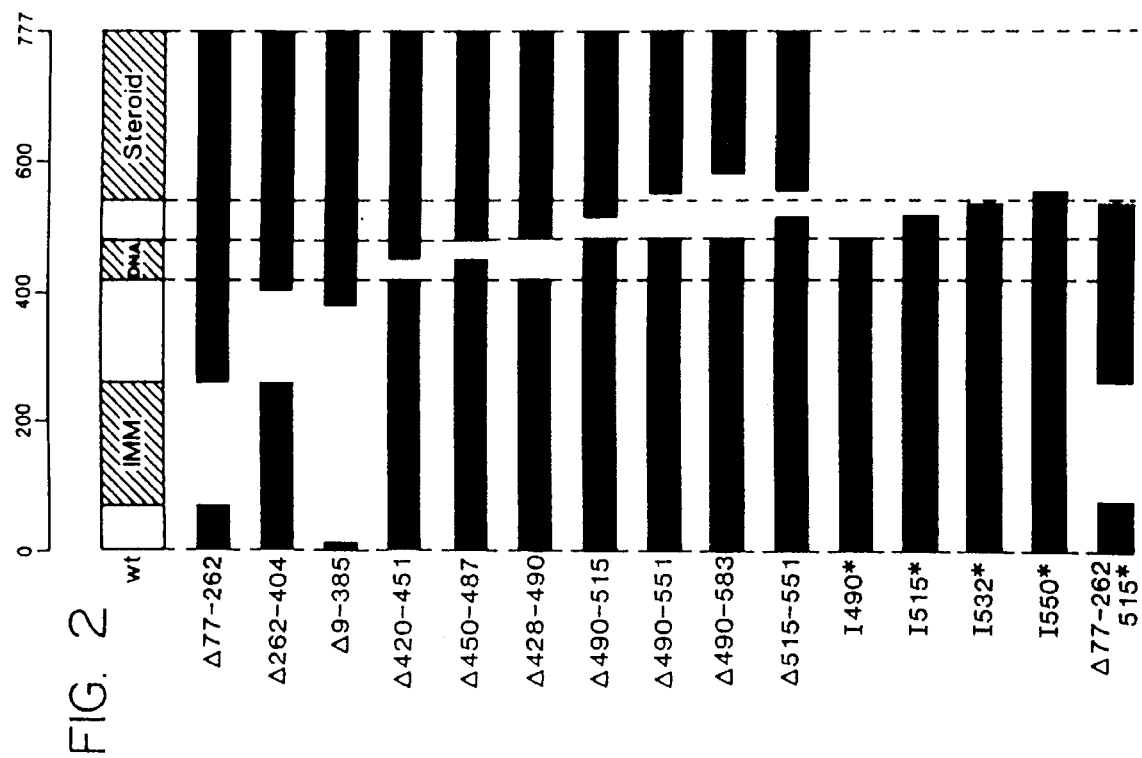
FIG. 2 presents the results of a scanning deletion analysis of the trans-repressing activity of hGR. Deletion mutants previously characterized for trans-activation (employing as a reporter plasmid one in which transcription of CAT is regulated by the hGR-responsive transcription regulatory segment (including promoter and GRE) of the mouse mammary tumor virus (MMTV)-LTR) (Hollenberg et al., supra.)), DNA binding and steroid binding were assayed on the alpha168 glycoprotein hormone transcription regulatory region (including the promoter and GRE) using the methods, reporter plasmids, RSV-promoter-containing control plasmid and cells described for FIG. 1 and using expression plasmids for the hGR or mutants in which transcription of DNA encoding such proteins was driven by the RSV promoter. The wild type receptor (wt) (i.e., naturally occurring receptor) comprises an immunogenic region (IMM), which coincides with the Tau1 region, a DNA binding domain (DNA), and a steroid-ligand binding domain (Steroid). The scale above the diagram of the wild-type receptor refers to amino acid number in the primary sequence of that receptor.
Figures 3A, 3B:
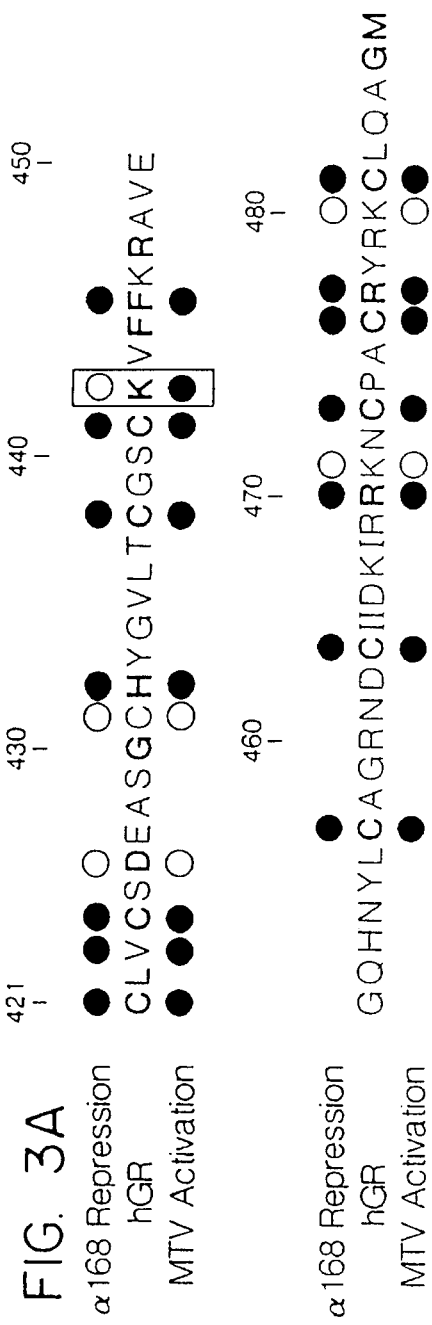

FIG. 3A and 3B presents the results of a study, carried out by the methods described for FIG. 2, of the trans-repression activity of mutants of the hGR in which an amino acid in the DNA-binding domain is changed to a glycine. The number of the changed amino acid in each of the mutants, in the primary sequence of the wild-type hGR, is indicated in the table (FIG. 3B)(with the prefix "G") along with the trans-repression activity (+/− the standard error of the mean of the results from the several experiments with the mutant) of the mutant with and without steroid (dexamethasone). In FIG. 3B, an asterisk indicates less than 10% of the trans-repression activity of the wild type hGR. (Wild-type hGR has no observable trans-repression or trans-activation activity in the absence of hormone.) The various mutants were previously assayed for trans-activation (Hollenberg and Evans, supra). In FIG. 3A, solid circles indicate activities less than 10 percent of wild type and open circles indicated activities greater than 10 percent of wild type activity in the presence of dexamethasone. The boxed residue in FIG. 3A represents the G442 mutant, which has a greater trans-repression activity than trans-activation activity. Bold residues in FIG. 3A are those conserved throughout the steroid hormone receptor family.

Figure 4:
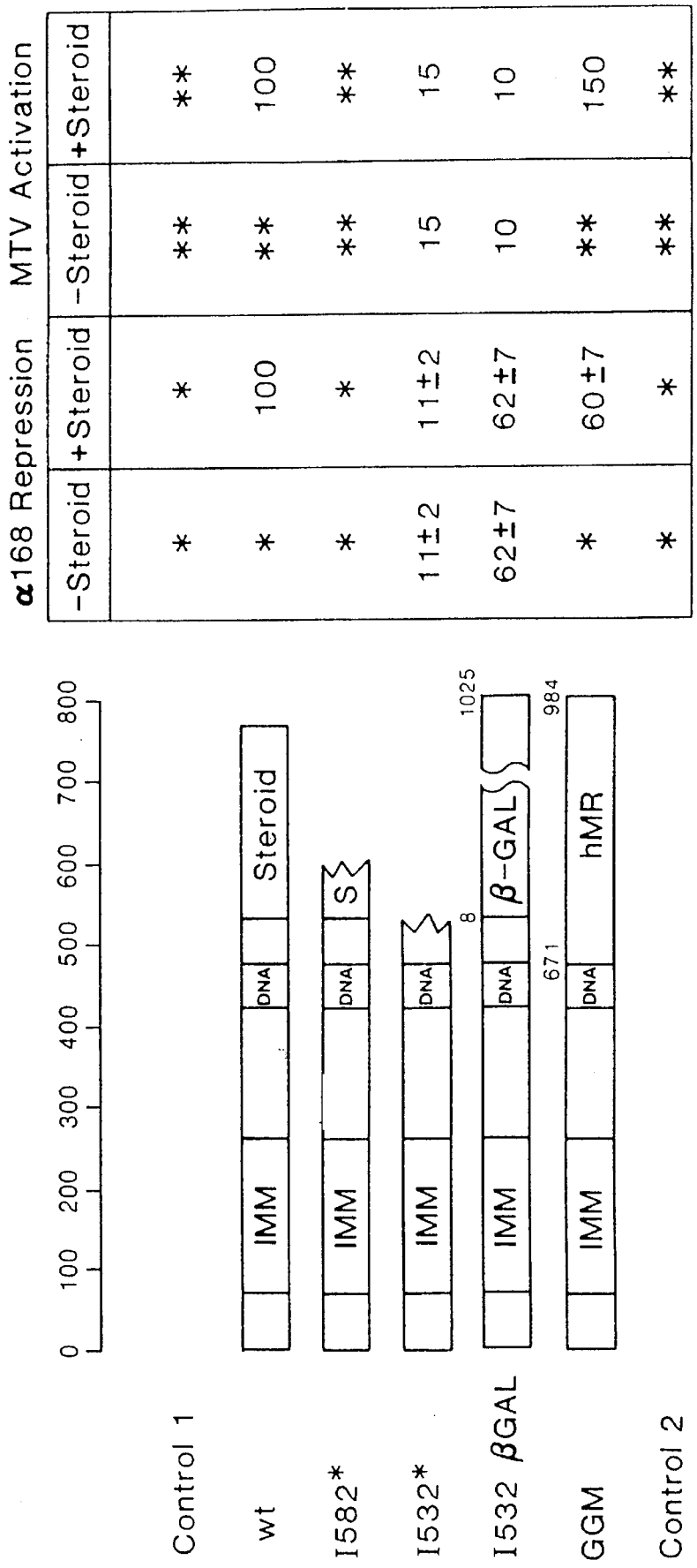

FIG. 4 represents the results of experiments on trans-repression and trans-activation activities of carboxy-terminal mutants of hGR. Such mutants include fusion proteins, with the carboxy-terminus of the wild-type hGR (by which is intended the part of the primary sequence of the receptor from amino acid 487 and higher, i.e., the part, including the ligand-binding domain, carboxy-terminal of the DNA-binding domain) replaced by a polypeptide of at least about 200 amino acids in length that, over the first 290 N-terminal amino acids, has less than about 60% amino acid identity with amino acids 487–777 of the hGR (the carboxy-terminal domain). Trans-activation and trans-repression activities were measured by the methods described above for FIGS. 2 and 3, except that the RSV plasmid used in controls 1 and 2 in place of the receptor- or receptor-analog-expressing plasmid had the thyroid hormone receptor-encoding cDNA inserted in the anti-sense orientation downstream of the RSV promoter rather than the beta-galactosidase-encoding DNA in the sense orientation (whereby beta-galactosidase was expressed). See Hollenberg et al., supra. The symbols in FIG. 4, that also occur in FIG. 2 or FIG. 3, have the same meanings as in FIG. 2 or FIG. 3. Mutant I532 beta-gal has the 1017 carboxy-terminal amino acids of beta-galactosidase (amino acid positions 8–1025) from plasmid pBG-1, a derivative of plasmid pSK105 (Casadaban et al., Meth. Enzymol. 100, 293 (1983)), fused in-frame to amino acid 532 of hGR. hGR mutant GGM consists of amino acids 1–489 of hGR as the N-terminal part and amino acids 671–984 of hMR (human mineralocorticoid receptor) as the C-terminal part. Mutant GGM was made from a cDNA constructed by first introducing an additional XhoI site into both the hGR-encoding sequence at position 1596 (Hollenberg, Weinberger, Ong et al., Nature 318, 635–641 (1985)) and the hMR-encoding sequence at nucleotide position 2233 (Arriza, Weinberger, Cerelli, et al., Science, 237, 268–275 (1987)) and then inserting the appropriate XhoI fragment of the hMR-encoding sequence into the appropriate XhoI site of the hGR-encoding sequence. With the wild-type hGR, control 1, and the three mutants other than GGM, the steroid used was dexamethasone. With the mutant with beta-gal at the carboxy-terminus, normalization for transfection efficiency was based on data from a plasmid in which luciferase was expressed from the RSV promoter, rather than the plasmid, described for FIG. 1 supra, in which beta-galactosidase is expressed from the RSV promoter. With GGM and Control 2, the steroid used was aldosterone. Control 2 was the same as Control 1 except for the substitution of aldosterone for dexamethasone.

GENERAL METHODS AN DEFINITIONS

Amino acid identification is by the standard single- and three-letter abbreviations. All amino acids (except Gly) are L-amino acids:

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

A steroid receptor analog of is prepared by expression of DNAs encoding the receptor analog, in mature form, or precursors thereof, said DNAs being part of expression vectors prepared by conventional techniques and used conventionally to transform cells to make the receptor analog (including embryonic cells to provide transgenic animals, at least some subset of cells of which make the receptor analog). A precursor of the receptor analog may 1) have methionine as the first amino acid (present by virtue of the ATG encoding the translational start signal in the DNA encoding the precursor) or 2) have a signal polypeptide or conjugated protein other than a signal polypeptide. As understood in the art, the methionine, signal peptide or conjugated protein other than a signal peptide is cleaved to yield the mature receptor analog. In all events, the thus produced mature receptor analog is either left, and used, inside the cell in which it is expressed or is recovered from the cell and purified to a level suitable for intended extracellular use.

The "hormone or hormone-like receptor analogs" of this invention or used in the methods of this invention include analogs of receptors of the steroid/thyroid hormone superfamily of receptors, including, among others, the glucocorticoid, mineralocorticoid, estrogen, progesterone, thyroid hormone, retinoic acid, and vitamin D3 receptors including such receptors from all species, including, among others, mammalian, including the human, species.

"Expression vector" means a vector which is capable of effecting expression of a DNA sequence contained in the vector once the vector has been transfected, transformed, microinjected or otherwise introduced into a suitable cell. In an expression vector, the DNA sequence to be expressed is operatively linked to other sequences capable of effecting the transcription of the DNA sequence along with other sequences, such that the transcript of the DNA sequence can be productively translated. A "suitable cell" for the vector is one in which these other, transcription-effecting sequences and the resulting translation-effecting sequences are recognized for transcription and translation. Construction of an expression vector of the invention and for use in accordance with the present invention is well within the skill of the person of ordinary skill in molecular biology, as are methods of introducing such a vector into cells suitable for expression of the DNA sequence intended to be expressed with the vector. An expression vector, in a suitable cell in which the vector is operative, can function as an episome or can be integrated into genomic DNA of the cell. An expression vector can be a circularized plasmid, a linearized plasmid or a part thereof, or all or part of a viral genome. Preferred for the present invention are expression vectors that are operative to effect expression of a DNA sequence in mammalian cells.

"Operative," or grammatical equivalents, for a particular purpose means, or refers to, means that are functional for the purpose. Thus, for example, "operatively linked for transcription" means linked by means (a DNA segment) that is functional in allowing transcription to occur.

"Recombinant host cells" refers to cells into which an expression vector, which will have been constructed by recombinant DNA methods, for a protein has been introduced by transfection, transformation, infection, microinjection or the like, or the progeny of such a cell which retain DNA that is capable of functioning to effect the expression of the protein.

Preparation of recombinant host cells and transgenic animals using expression vectors, from which receptor analogs of concern for the present invention are expressed, is well within the skill of those of ordinary skill in the art, as is the use of such cells and animals in screening compounds or other compositions for the purposes described hereinabove.

"Extrinsic support medium" includes those known or devised media that can support cells in a growth phase or maintain them in a viable state such that they can produce protein from DNA introduced using an expression vector (i.e., perform their "recombinantly harnessed function.") See, for example, *ATCC Media Handbook,* American Type Culture Collection, Rockville, Md. (1984 and later editions).

In addition to the above discussion and the various references to existing teachings in the art, reference is made to standard textbooks of molecular biology that contain definitions and methods and means for carrying out basic techniques in connection with the present invention. See, for example, Manjarls, et al, *Molecular Cloning: A Laboratory Manual,* Cold Spring Harbor Laboratory, New York, 1982 and the various references cited therein; Sambrook et al., *Molecular Cloning: A Laboratory Manual* (2nd Ed.), Cold Spring Harbor Laboratory, New York, 1989 and the various references cited therein; and Colowick et al., *Methods in Enzymology* Vol 152, Academic Press, Inc., New York, N.Y. (1987). All of the herein cited publications are incorporated herein by reference.

The description, including the following experimental details, in the present specification is intended to teach the invention and how to carry it out but not to limit the scope of the invention. It is understood, for example, that the skilled will readily recognize that they could employ different combinations of techniques, including techniques which the present inventors have not employed or described explicitly herein, to accomplish the same ends. Thus, for example, the skilled may synthesize the underlying DNA sequences encoding a particular novel receptor analog hereof for deployment within similar or other suitable, operative expression vectors and culture systems. Further, the skilled will readily recognize that they could apply the teaching of the present specification with analogs of receptors other than the human glucocorticoid receptor, which the present inventors elected to study as a prototype or model in making the present invention. The skilled will recognize that the present inventors, with their teaching herein, based on their discovery and elucidation, with analogs of the human glucocorticoid receptor as models, of the location, composition and mode of action in trans-repression, of domains involved in trans-repression, have provided a broad teaching of trans-repressing analogs of receptors of the steroid/thyroid hormone superfamily generally, including analogs in which domains from different members of the superfamily are combined, with or without modification.

DETAILED DESCRIPTION OF VARIOUS EMBODIMENTS

The present invention was premised upon use of the glucocorticoid receptor as a prototypical model, for the elucidation of the trans-repressing activity of receptors of the steroid/thyroid hormone superfamily of receptors, including glucocorticoid, mineralocorticoid, estrogen, progesterone, thyroid hormone-alpha, thyroid hormone-beta, retinoic acid, and vitamin D3 receptors, and for the identification, based on such elucidation, of trans-repressing analogs, including certain novel analogs, of such receptors. Particularly sought were trans-repressing analogs that have trans-repressing activity (measured relative to that of the corresponding native ("wild-type") receptor that is greater than trans-activating activity (also measured relative to that of the corresponding native receptor), and especially analogs in which the trans-repressing activity is increased relative to that of the native receptor and the trans-activating activity is decreased relative to that of the native receptor. These especially preferred analogs can confer on a cell in which they are expressed the phenotype in which the function of the hormone corresponding to the native receptor is dominantly repressed.

The present specification teaches those of ordinary skill how to identify readily trans-repressing analogs of such receptors, including such analogs with the more desirable properties.

As outlined, supra, analogs with trans-repressing activity greater than trans-activating activity, and especially those with trans-repressing activity increased over, and trans-activating activity reduced below, that of the corresponding native receptor, may be especially usefully employed in gene therapy, to remedy a disease due inability to properly process the hormone of the corresponding native receptor, and in screening, with cells in culture or transgenic animals, for compositions effective to treat diseases due to inability to properly process the hormone of the corresponding native receptor. In the latter application, transgenic rodents, and especially transgenic mice, are especially preferred. Among such diseases that may be remedied, or for which therapeutically effective compositions may be identified, in accordance with these novel methods of use of the present invention, novel cells of the invention, and novel, non-human transgenic animals of the invention, are various disorders, including manic depressive disorders, immune system disorders, and growth-related disorders, due to the inability to properly process glucocorticoids; pseudohypoaldosteronism, characterized by inability to properly process aldosterone; and erythroblastoid leukemias and the various manifestations of Cretinism, which are due to the inability of cells to properly process thyroid hormone.

EXAMPLES

Certain experimental details are described above, in connection with description of the Figures, and are not repeated here.

Recombinant Plasmids

I515* GR (glucocorticoid receptor) and delta-77-262 GR are prepared as described by Hollenberg et al., *Cell* 49, 39 (1987).

Mutant delta-77-262,I515* GR was made by swapping the ClaI-XhoI fragment of the mutant I515* with that of delta-77-262 GR mutant.

The construction of the alpha168CAT, with the alpha168 glycoprotein hormone promoter and associated regulatory elements including a GRE, driving expression of CAT, has been described by Delegeane et al., Mol. Cell Bio 7, 3994 (1987)).

Transfections and Reporter Assays

JEG-3 human placental cells were maintained in DMEM (Dulbecco's Modified Eagles' Medium), 10 percent defined calf bovine serum (CBS), and 0.4 percent glucose and split 24 hours prior to transfection into 5 percent CBS charcoal-stripped serum plus glucose (Akerblom et al., *Science* 241, 350 (1988)). Transfections were performed in JEG-3 cells via the calcium phosphate precipitation method (Delegeane et al., supra (1987)). Typically, 2 µg of reporter and 4 µg of receptor plasmid were used along with 2 µg of RSV β-gal (Hollenberg et al., supra (1987)) as an internal control for transfection efficiency. Dexamethasone and aldosterone ($10^{-7}$ M) were added after calcium phosphate treatment. CAT assays were performed according to Hollenberg et al., supra (1987), but with 25 µg total cell extract protein for 3 hours or less. TLC plates were cut and counted in Econofluor +5 percent DMSO. Luciferase and beta-galactosidase, produced from plasmids used to provide data for normalization for transfection efficiency, were assayed by standard methods.

hGR Trans-repression

Figure 1:
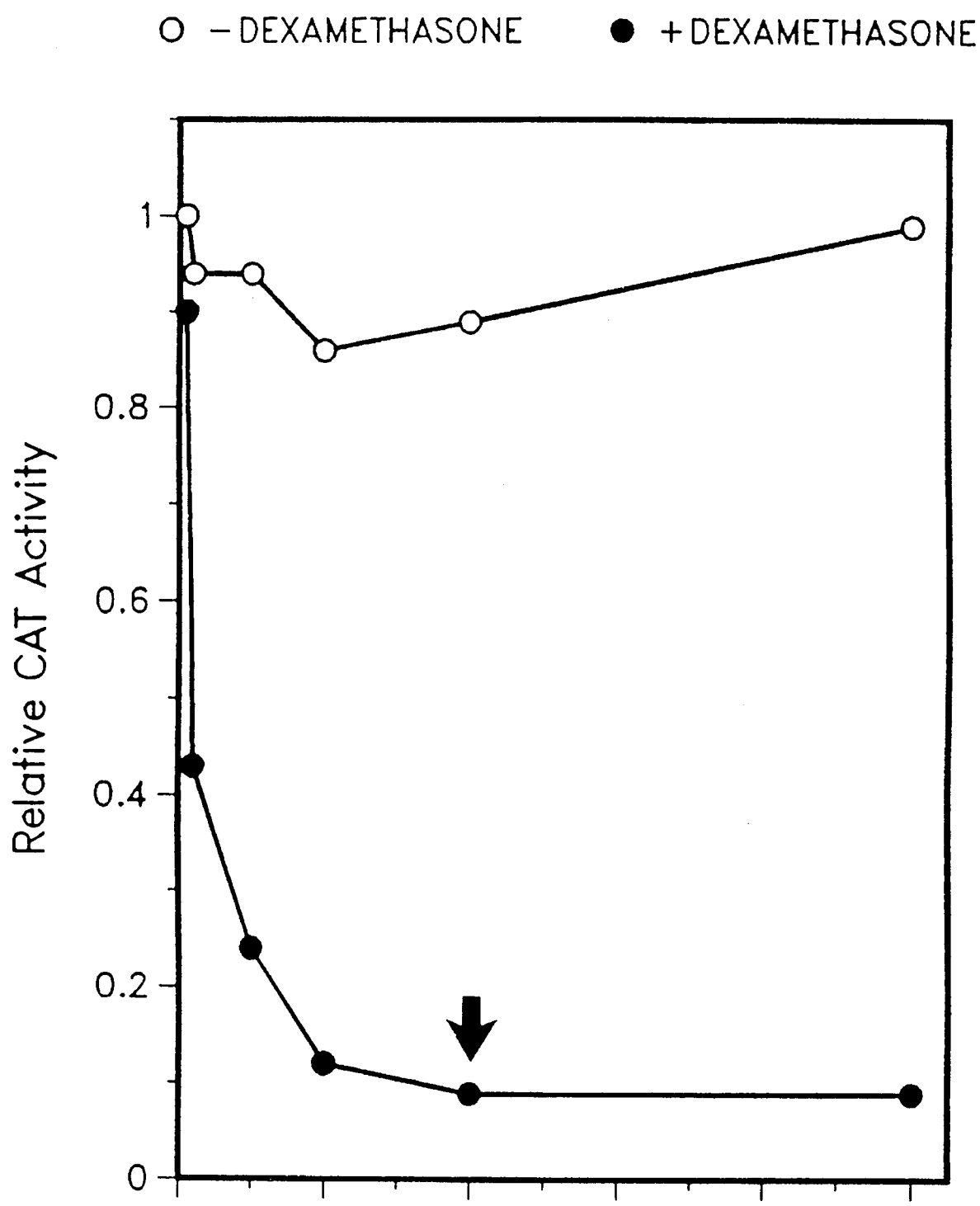
FIG. 1 is a dose response curve for hGR (human glucocorticoid receptor)-mediated repression of transcription. An hGR expression plasmid, wherein transcription of a cDNA encoding the hGR is driven by the rous sarcoma virus (RSV) promoter, was cotransfected into JEG-3 human placental cells (Akerblom et al., supra), with a reporter plasmid in which transcription of DNA encoding CAT (chloramphenicol acetyltransferase), as the reporter or indicator protein, is driven by a transcription regulatory element which includes, from the regulatory element that controls transcription of the alpha168 glycoprotein hormone promoter, the DNA segment that includes the alpha168 glycoprotein hormone promoter and the glucocorticoid receptor response element (GRE), to which the naturally occurring hGR (when complexed with glucocorticoid hormone) binds. The co-transfection was by the calcium phosphate precipitation method. In different cultures, the ratio of hGR-encoding plasmid to reporter plasmid (referred to in the Figure as "promoter plasmid") used in the co-transfection was different. The total molar amount of RSV promoter DNA transfected was kept constant by replacing hGR-encoding plasmid with a control plasmid, which was an RSV-promoter-containing expression plasmid, in which transcription of beta-galactosidase was driven by the RSV-promoter. The CAT activity from the reporter plasmid was measured as described in experimental procedures and normalized for transfection efficiency by dividing by the activity of beta-galactosidase provided by the control plasmid. Open circles indicate media without dexamethasone, solid circles media with $10^{-7}$ M dexamethasone. In the particular experiment for which results are given in FIG. 1, 2 μg of reporter plasmid was used. The arrow indicates the ratio of receptor-encoding plasmid to reporter plasmid used in subsequent experiments.

To characterize the hGR-mediated repression, a dose response curve was performed of hGR expression plasmid for negative regulation of the alpha 168 CAT expression in human placental JEG-3 cells. Varying amounts of the hGR expression plasmid and alpha168 CAT plasmid were cotransfected, and the resultant transient CAT activity plus and minus dexamethasone was measured. Throughout the experiment the total amount of RSV promoter was constant, thus controlling for possible titration of transcription factors by RSV DNA. FIG. 1 shows the hormone-dependent reduction in gens expression with the transfection of exogenous receptor cDNA into cells with the alpha168 glycoprotein hormone transcription regulatory apparatus.

Increasing amounts of the receptor expression plasmid yielded a correspondingly higher steroid-dependent repression of transcription from the alpha168 promoter. In the absence of receptor cDNA, less than 10 percent of maximal repression can be measured. Beginning at a receptor to promoter ratio of 1 and continuing to a ratio of 5, a plateau of repression activity emerged where more receptor plasmid yielded no additional steroid-dependent repression. Since the amount of RSV promoter was held constant, this plateau indicates probable saturation of the site of receptor action. For subsequent experiments, for which results are presented in the Figures, a receptor to promoter ratio of 2:1 was used. The steroid-dependent repression of alpha168 reporter observed with wild-type hGR varies between 6 and 20 fold with an average of 9 fold as typified in FIG. 1. This assay can reliably measures as low as 10 percent of wild type hGR repression.

Distinct Activation and Repression Domains

Various hGR mutants were tested in the repression assay and compared to their activities in the MTV activation assay. FIG. 2 shows a comparison of repression activity by various hGR mutants on the alpha168 promoter compared to activation on the MTV promoter. Deletions in the amino terminus (i.e., the part of the native receptor that is in the amino-terminal direction from the amino-terminus of the DNA-binding domain or, in the case of hGR, the part of the mature receptor from amino acids 1–420) had no adverse effect on repression activity. In fact, amino-terminal mutants, including those lacking up to 376 amino terminal residues, displayed increased dexamethasone-dependent repression in comparison with the native receptor and unchanged, or marginally increased, repression activity with mutant receptors which retain transcription-altering activity but are altered outside the N-terminal domain. For example, deletion of the trans-activation-related sequence Taul (amino acids 78–261), that roughly coincides with the immunogenic region (IMM), in the mutant designated delta-77-262, increases trans-repression activity to 140 percent of wild type activity while dramatically reducing trans-activation activity at the MTV promoter to 10 percent of wild-type. Compare also mutant delta-77-262, I515* (the bottom entry in FIG. 2) with mutant I515*. These results demonstrate that the amino terminus of a receptor of the steroid/thyroid hormone receptor superfamily (i.e., the part of the receptor N-terminal from the N-terminus of its DNA-binding domain) plays reciprocal roles in repression and activation and that receptor analogs that differ from the corresponding native receptor or mutants thereof only in a deletion in the amino-terminus will have at least the same trans-repressing activity as the corresponding native receptor or mutant, on a promoter which is trans-repressed by the native receptor or mutant, and will have significantly reduced trans-activation activity on a promoter, which is trans-activated by the native receptor or mutant.

DNA-Binding Domain Required for Repression Activity

The DNA-binding domain of the hGR is cysteine-rich and has been proposed to be comprised of two zinc fingers, as described supra. The presence of a DNA-binding domain is necessary since insertions in or deletions from this region (mutants delta-420-451 (missing amino acids 421–450, the first zinc-finger), delta-450-487 (missing amino acids 451–486, the second zinc-finger), and delta-428-490 (missing amino acids 429–489, most of the DNA-binding domain) (FIG. 2) yield receptor variants that are incapable of both trans-repression and trans-activation. Both zinc fingers are required for trans-repression as well as trans-activation.

Nineteen (19) receptor variants, each harboring one amino acid change (a glycine for the numbered amino acid) in the DNA-binding domain, were comparatively evaluated for their trans-repressor and trans-activator activities (FIG. 3). Most of the mutants have corresponding effects on both repression and activation. For example, mutants in residues 480 and 431, (labeled G480 and G431, respectively), reduce both repression and activation to 70 percent of their wild type values while G438 and G445 eliminate both activities. 18 of the 19 mutants show parallel effects on activation and repression. In contrast, one mutant, G442, retains 68 percent of full repressor function while it activates only 1 percent. Moreover, this lysine-to-glycine mutant binds hormone and DNA in vitro with nearly normal activity. Apparently, it is the retention of its DNA-binding capacity that allows the mutant to remain active in trans-repression although trans-activation requires, in addition to DNA binding, a function lost in the mutant.

Carboxyl Terminus Enhances Repression

Truncation deletion-mutants reveal that the carboxyl terminus (the part of the receptor carboxy-terminal from the carboxy-terminal end of the DNA-binding domain) plays an important role in both negative regulation (i.e., trans-repression) and activation (i.e., trans-activation). The carboxy-terminal part of an hormone or hormone-like receptor of the steroid/thyroid hormone superfamily has two sub-domains: the ligand-binding subdomain and an "hinge-subdomain," which joins the carboxy-terminus of the DNA-binding domain to the amino-terminus of the ligand-binding domain. The following Table 5 lists the approximate boundaries of these sub-domains for representatives of this superfamily of receptors:

TABLE 5

| Receptor | First Amino Acid of Hinge Subdomain | First Amino Acid of Ligand-binding Subdomain |
|---|---|---|
| Human Glucocorticoid | 487 | 528 |
| Human Mineralo-corticoid | 669 | 734 |
| Human Thyroid Hormone Beta (c-erbA gene protein) | 169 | 232 |
| Rat Neuronal Thyroid Hormone (Alpha) | 120 | 183 |
| Human Estrogen | 251 | 311 |
| Rabbit Progesterone | 634 | 680 |
| Human Retinoic Acid | 154 | 198 |
| Human Vitamin D3 | 90 | 192 |

With respect to the data in Table 5, see the published patent applications cited at the beginning of the present specification.

Several receptors of the steroid/thyroid hormone superfamily are known to have subsegments, that are apparently not related to ligand-binding and are located carboxy-terminal of the carboxy-terminal end of the ligand-binding subdomain. However, for purposes of the present specification, these additional subsegments are deemed to be part of the ligand-binding subdomain of the carboxy-terminal domain. In this regard, also see the published patent applications cited at the beginning of this specification.

As shown in FIG. 2, mutant I490* truncates the receptor at amino acid 490 adjacent to the DNA binding domain and has lost both repressor and activator functions. Deletions or truncation that intrude on the ligand-binding domain (for example, delta-515-551, delta-490-583, I582, in FIG. 4) eliminate DNA and hormone binding and also completely eliminate both activities. In contrast, deletions in the region linking the DNA binding and ligand binding domains (delta-490-515) retain near wild-type, steroid-dependent repression and activation. Further, truncation mutants I550* and I532* remove the entire ligand binding domain and engender analogs that are both constitutive (i.e., ligand-independent) repressors and activators. Truncation mutant I550* reduces the repression to 30 percent of wild type with I532* retaining only marginal repressor function. These results suggest the requirement of an intact ligand binding subdomain and at least about the 10 carboxy-terminal amino acids of the hinge subdomian for retention of most (i.e., more than about 50% of wild-type) of trans-repression and trans-activation activities and localize an important domain for trans-repression activity to the carboxyl terminal amino acids of receptors of the steroid/thyroid hormone superfamily.

Fusion Repressors

At least two mechanisms exist to explain the role of the carboxyl-terminus in trans-repression. First, a particular region of the carboxyl terminus could interact specifically with an activator to block or mask transactivation properties and thereby effect trans-repression. Secondly, the carboxyl terminus could mediate its effects by stearic hindrance as has been shown in procaryotic systems, blocking the interaction of transcription factors near their sites of action on DNA or the interaction of cooperatively acting proteins with each other.

Novel sequence specific repressors were created by attaching heterologous protein sequences to the carboxyl terminal side of the hGR DNA binding domain. In the first case, the hinge and ligand binding subdomains of a related steroid receptor (hMR) was substituted for the homologous region of the hGR. This hybrid receptor, as shown in FIG. 4, becomes an aldosterone-dependent activator of the MTV promoter and an aldosterone-dependent repressor of the alpha 168 promoter. Thus, the hMR carboxyl terminus is able to substitute for both activator and repressor functions. Although aldosterone is not known to naturally influence the expression of the alpha168 promoter, one could argue that the amino acid homology of these steroid receptors represents evolutionary selection for several functions including trans-repression. To address this possibility, E. coli β-galactosidase (β-gal) was fused in frame to the carboxyl terminal side of the hGR DNA-binding domain and assayed for regulatory properties. On the MTV promoter this hybrid functions as a constitutive activator with properties unchanged from that of the parental truncated receptor (I532*). On the alpha168 promoter, the fusion protein is a constitutive repressor whose activity is dramatically increased when compared to that of I532*. Thus, the addition of a heterologous E. coli protein sequence to the DNA binding domain of the hGR is sufficient for generation of a functional transcriptional repressor.

Our data show that activation and repression by hGR share some common features. First, the results demonstrate a requirement for the DNA-binding domain in hGR-mediated repression. This reflects the fact that both positive and negative regulation are DNA sequence-specific. The result that 18 out of 19 point mutations in this region affect repression and activation equivalently argues that this domain is serving a common function in each process. Further, because many of these 18 mutations affect DNA-binding, we deduce that the same amino acids are critical for recognition of response elements mediating both activation and repression. Secondly, the carboxyl terminal deletions show that activation and repression at near wild-type levels require an intact ligand binding domain and the presence of hormone. Removal or replacement of this region by heterologous sequences leads to hormone independence for both processes.

In contrast, the results of this study provide several criteria that distinguish positive and negative regulatory effects of the hGR. First, the amino terminal domain that contains a potent activator sequence (Tau 1) is not necessary for trans-repression. This fact substantiates the duality of receptor function and is highlighted by the observation that deletion of Tau 1 engenders a more potent repressor. This argues that even when functioning as a repressor, the amino terminal region of the hGR retains some residual activating activity.

The DNA-binding domain mutation, G442, establishes a second criterion distinguishing the two processes. The mutation produces a receptor that retains significant trans-repression activity but has lost virtually all trans-activation capability. This result demonstrates that the process of activation can be mechanistically distinguished from that of repression and that the function of the DNA-binding domain is more than simply to locate an appropriate regulatory sequence. Moreover, the result also implies that activation requires an additional event subsequent to DNA-binding that is apparently not critical for repression.

A third criterion differentiating activation and repression is that a β-galactosidase moiety functionally replaces the hGR carboxyl terminus only in repression. Removal of the ligand-binding subdomain results in a receptor variant with minimal repression activity. The role of this region might be explained by two models. First, it might directly interact with other transcription factors to block or neutralize their transactivation domains. Secondly, it might non-specifically inhibit activation by preventing other factors from binding to DNA or interacting with the transcription machinery. The latter stearic hindrance model is supported by the fact that addition of a β-galactosidase moiety selectively increases repression and not activation, while additional of an hMR carboxyl terminus increases both activities. Given the lack of amino acid identity or similar charge distribution between the hGR, hMR and β-gal, a role for specific interaction with another transcription factor is unlikely. A reasonable property conserved between the carboxyl termini of hGR and the two fusion proteins is relative size. I532* lacks 245 carboxyl terminal amino acids of the wild type hGR, whereas the hGR-hMR and the hGR-β-gal fusions add 310 and 1030 amino acids, respectively. In contrast to previously characterized trans-activation or trans-repression domains where charge distribution or a conserved amino acid sequence is important, hGR trans-repression domains appear to require molecular volume.

Any process which requires the proximity of two transcription factors can be repressed by stearic hindrance. On the alpha168 promoter, basal expression requires both CRE and TSE binding proteins as well as factors binding to CCAAT and TATA sequences (Akerblom et al., 1988, supra). The displacement or prevention of any of the proteins bound to their elements would reduce transcription. The footprinted hGR binding sites cover the TSE/CRE border and support an interaction between the hGR, and the TSE and CRE binding proteins; lack of the TSE drops basal expression 8–10 fold (e.g., the 152–100 tk cat promoter construction (Akerblom et al., 1988, supra)), and reduces basal level hGR-mediated repression.

It is possible to create fusion repressors because the DNA-binding domain, and other domains associated with trans-activation and trans-repression, are functionally largely independent and structurally distinct. These results suggest a general strategy to produce sequence-specific transcription repressors, with the sequence specificity provided by a DNA-binding domain.

The fact that the foregoing description is somewhat detailed should not be construed as limiting the overall scope hereof; rather, the ambit of the present invention is to be governed only by the lawful construction of the appended claims.

We claim:

1. A trans-repressing analog of a receptor of the steroid/thyroid hormone superfamily of receptors, wherein said analog comprises an amino acid sequence having the N-terminus and DNA binding domain of a receptor of the steroid/thyroid superfamily of receptors fused at its C-terminal end to amino acids 8–1025 of beta-galactosidase.

2. A trans-repressing analog of a receptor of the steroid/thyroid hormone superfamily of receptors, wherein said analog is I532-beta-gal.

3. An expression vector capable of expressing the receptor analog of claim 1.

4. An expression vector capable of expressing the receptor analog of claim 2.

5. A recombinant host cell transfected with an expression vector according to claim 1.

6. A recombinant host cell transfected with an expression vector according to claim 2.

7. A cell culture comprising cells according to claim 1 and an extrinsic support medium assuring the viability of the cells in culture.

8. A cell culture comprising cells according to claim 2 and an extrinsic support medium assuring the viability of the cells in culture.

* * * * *